United States Patent
Dunkley

[11] Patent Number: 6,115,873
[45] Date of Patent: Sep. 12, 2000

[54] APPLICATOR FOR LOTIONS

[75] Inventor: Graham William Miles Alway Dunkley, Brookthorpe, United Kingdom

[73] Assignee: Synlatex Limited, Gloucester, United Kingdom

[21] Appl. No.: 09/120,312

[22] Filed: Jul. 22, 1998

[30] Foreign Application Priority Data

Jul. 22, 1997 [GB] United Kingdom .................... 9715284

[51] Int. Cl.[7] ...................................................... A47K 7/02
[52] U.S. Cl. ........................... 15/227; 15/209.1; 15/210.1
[58] Field of Search ................... 15/227, 210.1, 15/229.14, 229.11, 229.12, 229.13, 244.3, 208, 209.1

[56] References Cited

U.S. PATENT DOCUMENTS

| | | |
|---|---|---|
| 1,193,529 | 8/1916 | Ellis . |
| 1,528,026 | 3/1925 | Pease . |
| 1,884,659 | 10/1932 | Gould . |
| 4,670,930 | 6/1987 | Lu . |
| 4,953,250 | 9/1990 | Brown . |
| 5,134,746 | 8/1992 | William . |
| 5,815,876 | 10/1998 | Overseth . |

FOREIGN PATENT DOCUMENTS

| | | |
|---|---|---|
| 0 086 355 | 8/1983 | European Pat. Off. . |
| 0 245 983 | 11/1987 | European Pat. Off. . |
| 0 409 802 | 1/1991 | European Pat. Off. . |
| 1 174 337 | 12/1969 | United Kingdom . |
| 1 596 620 | 8/1981 | United Kingdom . |

*Primary Examiner*—Terrence R. Till
*Assistant Examiner*—Jennifer McNeil
*Attorney, Agent, or Firm*—Young & Thompson

[57] ABSTRACT

An applicator for lotions comprises two layers of flexible material joined together to form a mitt into which at least a part of a user's hand maybe inserted. One or both layers each comprises a flexible synthetic foam material to the outer surface of which is applied a layer of flock. In use, the user inserts her hand or fingers between the two layers of the applicator and applies lotion to the flock-faced outer surface of the foam layer which is at the front of the hand. The lotion may then be applied to the skin without the user's hand coming into contact with it, and the combination of the flexible foam material with the layer of flock enables the lotion to be applied smoothly and easily over a large area.

30 Claims, 1 Drawing Sheet

APPLICATOR FOR LOTIONS

BACKGROUND OF THE INVENTION

The invention relates to applicators for lotions and provides an applicator which is particularly, but not exclusively, suitable for the application of self-tanning lotions to the skin.

As is well known, an artificial tan may be applied to a person's skin by applying a lotion containing a pigment which, whey dry, simulates the colour of sun-tanned skin. Some lotions apply the colour immediately to the skin, whereas others have a formula such that the colour develops on the skin subsequently.

In order to provide a realistic effect, such lotions have to be applied evenly over large areas of the person's body. Hitherto, it has been the usual practice to apply such lotions with the bare hands. However, such method has certain disadvantages.

Firstly, it may not be easy to apply the lotion evenly to the skin, using the hands and fingers alone, with the result that the colour may have darker or lighter patches and streaks, giving an unrealistic visual effect. Secondly, it is inevitable that substantia residues of the lotion will remain on the user's hands, and since the very purpose of the lotion is to colour any skin surface to which it is applied, the palms of the user's hands may often acquire a very dark and unrealistic coloration. This unwanted colour may be difficult to remove since it is obviously a desirable feature of such lotions that the suntan effect they provide should not readily disappear with washing.

The present invention therefore sets out to provide an applicator, suitable for use with such lotions, which enables the lotion to be applied over large areas both quickly and evenly, while at the same time preventing the lotion coming into contact with the user's hands during such application.

SUMMARY OF THE INVENTION

According to the invention there is provided an applicator for lotions comprising two layers of flexible material joined together in a manner to allow insertion of at least a part of a user's hand between the layers, at least one of said layers comprising a flexible synthetic foam material to the outer surface of which is applied a layer of flock.

As is well known, flock comprises an area of closely-packed fibres, each fibre being attached at one end to the surface of the supporting layer so that the fibres are generally parallel and upstand from the supporting layer to give the effect of a pile.

In use, the user inserts her hand (or two or more fingers only, depending on the size of the applicator) between the two layers of the applicator and applies lotion to the flock-faced outer surface of the foam layer which is adjacent the palm of the hand. The lotion may then be applied to the skin without the user's hand coming into contact with it, and the combination of the flexible foam material with the layer of flock makes it easy to apply the lotion smoothly and easily over a large area.

Preferably both layers of the applicator each comprise a flexible synthetic foam material to the outer surface of which a layer of flock is applied. This enables either side of the applicator to be used for the application of lotion.

The two layers may have coincident side edges which are secured together in a manner to allow insertion of the user's hand between the layers. The two layers may be substantially co-extensive. In this case the co-extensive layers may be secured together around substantially three sides thereof, leaving a fourth side into which a user's hand may be inserted, the applicator then being generally in the form of a mitten.

Although the mitten may be shaped to have a portion to receive the thumb of the user, it is found that the applicator may be more effective without such a portion, the fingers and thumb being all received into a single region between the layers. Alternatively, the applicator may be of such a size that only two, three or four of the user's fingers may be inserted between the layers.

In one particular form of the invention, the applicator may comprise an open edge, for the insertion of at least part of the user's hand, where ,he layers are not joined together, two joined side edges extending away from opposite ends respectively of the open edge, and a convexly curved joined end edge extending between the ends of the side edges remote from the open edge.

Preferably the curved end edge is part-circular in shape and the side edges are tangential to the end edge so as to form smooth extensions thereof. Preferably the side edges diverge as they extend away from the open edge.

Alternatively, instead of the two layers being substantially coextensive, one layer may be smaller than the other and extend across only a portion of the other layer. For example, one layer may be in the form of a strap or pocket extending across only a part of the other, larger layer. The user's hand or fingers are then inserted beneath the strap or into the pocket. In this case the larger layer comprises said flexible synthetic foam material to the outer surface of which is applied a layer of flock.

The layers may be secured together by stitching, adhesive, welding, such as ultrasonic, high frequency, or heat welding, or by any other suitable means. Any combination of such means may be employed.

The foam layer, or both layers, may be formed from flexible polyurethane/polyester foam, and the flock may be attached directly to the surface of the foam by a suitable adhesive.

The flock may comprise rayon/viscose fibres, which may be of any suitable length. For example, the fibres may have a length in the range of 0.20–1.00 mm. A preferred length of fibre is about 0.5 mm.

The foam may be of any suitable thickness. For example, the foam may have a thickness in the range of 2–6 mm. A preferred thickness is about 4.3 mm.

The foam may be of a kind which is substantially non-permeable to liquid. If the foam is of a kind which is permeable, or semi-permeable, to liquid, there is preferably applied to the foam a layer of liquid-impermeable material to prevent liquid migrating inwardly from the outer surface of the applicator to the inner region between the layers. The liquid-impermeable layer may be applied to either side of the foam layer. For example, the liquid-impermeable layer may comprise the adhesive by which the flock is adhered to the foam, or an additional layer between such adhesive and the foam. Preferably, however, the layer of liquid-impermeable material is applied to the inner surface of the foam. For example, it may be applied as a coating of a settable liquid which permeates the foam adjacent the inner surface thereof.

DETAILED DESCRIPTION OF THE PREFERRED EMBODIMENTS

Figure 1:
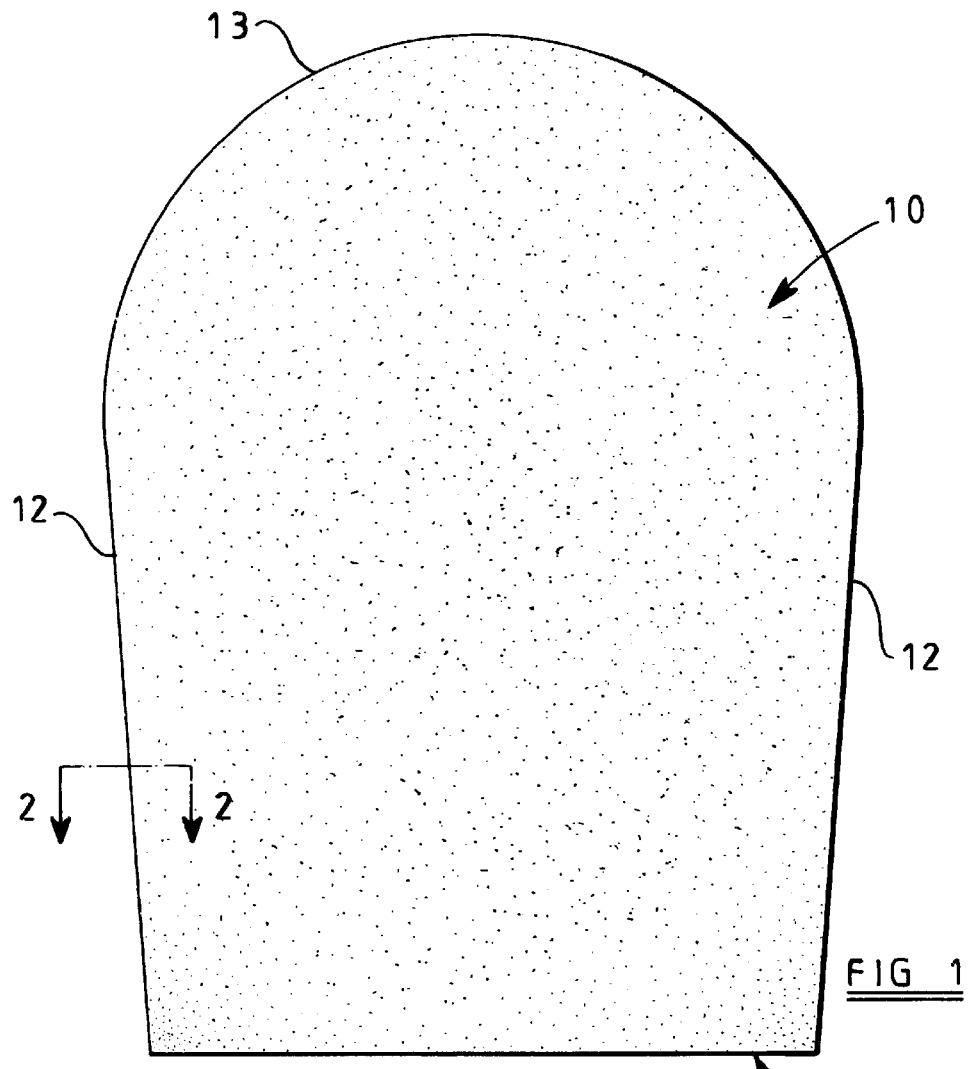
FIG. 1 is a plan view of one form of applicator in accordance with the invention.

Referring to the drawings: the applicator is in the form of a mitten 10. The mitten has an open edge 11 through which a user's hand may be inserted, side edges 12 which diverge slightly as they extend away from the open edge 11, and a generally semi-circular end edge 13 to which the side edges 12 are tangential so as to form smooth continuations thereof.

The length of the open edge 11 may be of the order of 110 mm and the length of the mitten from the open edge 11 to the furthest extremity of the curved edge 13 may be of the order of 200 mm. The width of the mitten, at its widest point, may be of the order of 125 mm.

Figure 2:
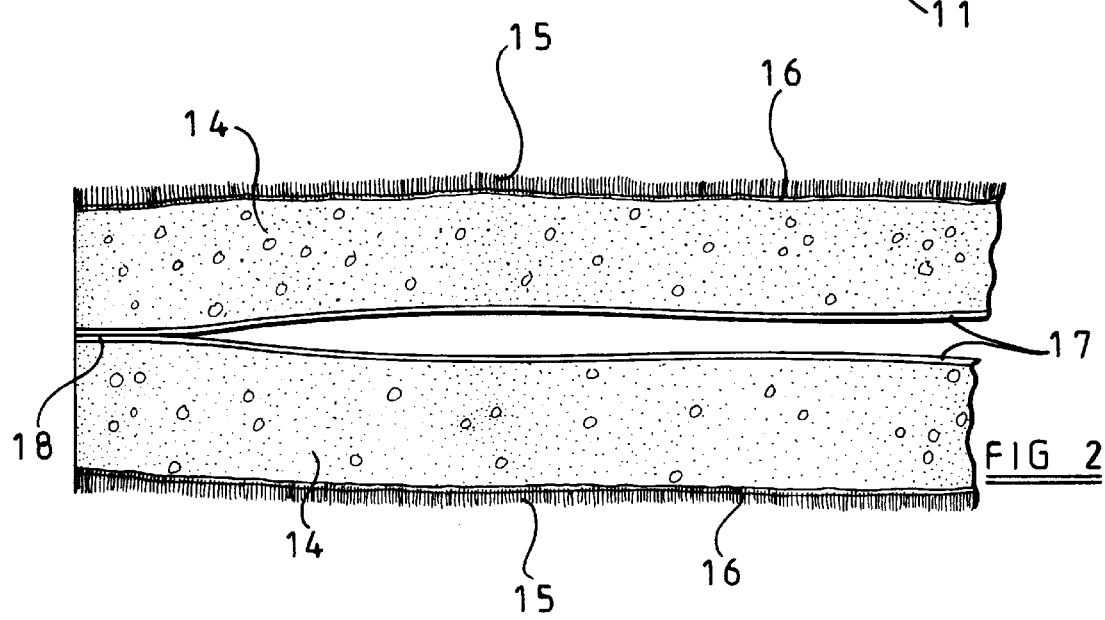
FIG. 2 is a diagrammatic section, on an enlarged scale, through a side edge portion of the applicator shown in FIG. 1, taken along the line 2—2 of FIG. 1.

Referring to FIG. 2, it will be seen that the mitten comprises two layers of polyurethane/polyester foam 14 to the outer surface of each of which is applied a layer of closely packed flock fibres 15 secured to the foam 14 by an adhesive layer 16. A coating of liquid-impermeable material 17 is applied to the inner surface of each foam layer 14.

The inner layer 17 is, for the purposes of illustration, shown diagrammatically as a distinct layer in FIG. 2, but in practice the layer 17 may be applied to the inner surface of the foam 14 in liquid form so that it permeates into the cells of the foam before setting.

Except for the open edge 11, the two layers 14 of the mitten are secured together around its periphery, as indicated at 18 in FIG. 2, by ultrasonic welding or heat welding, both of which techniques are well known and will not be described in detail. Alternatively, the layers could be secured together by stitching, by an adhesive or by any other means or combination of means.

The mitten may be manufactured by first manufacturing a sheet material comprising, in combination, the foam layer 14, the flock 15 applied to one surface, and the liquid-impermeable coating applied to the other surface. Two layers of such sheet material are then placed back-to-back, with the liquid-impermeable coatings 17 in contact with one another. The two layers are then passed through a die-cutting machine in which suitably-shaped dies cut the two layers into the shape shown in FIG. 1. Preferably, the die cutting machine is arranged to weld the peripheral edges of the cut layers together at the same time as they are cut. Alternatively, the layers may be secured together subsequently.

Each layer of foam 14 may have a thickness of 4.3 mm, but although this thickness is preferred, other thicknesses of foam may be employed, for example in the range of 2–6 mm. The poyurethane/polyester foam may have the following characteristics.

Density (Kg/m$^3$): 24.0–27.0

Tensile Strength (kPa): 160–500

Elongation at Break (%) 250–600

50% Compression Set (%): 0–10.0

Cell Count (per cm): 18–26

40% CLD Hardness (kPa): 2.5–4.5

The flock may comprise fibres of cotton, rayon, nylon, acrylic or any other appropriate fibre, although rayon/viscose fibre is preferred. The adhesive layer may be a modified co-polymer. The length of the fibres is preferably 0.5 mm, this being found to be most suitable for the application of self-tanning lotions. However, other lengths of fibre may be employed if desired, for example in the range of 0.2–1.00 mm. The method of applying flock to the surface of a base material, such as the foam layers 14, is well known and will not therefore be described in detail. The flock may be of any suitable colour, such as peach.

The liquid-impermeable coating applied to the inner surface of the layers may be the clear lotion repellent sold under the trade mark Tivoflex ref: 3560/1. The coating may be applied by rollers or may be sprayed onto the foam.

The above-described form of applicator is by way of example only, and many modifications may be made to the specific design without departing from the scope of the invention. For example, although the mitten is shown as being double-sided, this is not essential, and only one side of the mitten might be formed of the flocked foam for applying lotion. The other side of the mitten could then be any other fabric or flexible sheet material. Also, the invention does not exclude arrangements where the applicator is not in the form of an enclosed mitten, but where the application layer is backed by a smaller area or strip of fabric which passes over the back of the user's hand to hold the applicator in place when the palm of the hand is applied to the inner surface of the application layer.

The applicator may be of any suitable size and shape, depending on the desired use. Although the example described above is of such a size that the whole of the user's hand may be inserted into it, smaller sizes are possible where only two, three or four of the user's fingers are inserted in use. For example, a smaller applicator which fits on only two fingers may be more suitable for applying lotion to the user's face.

What is claimed is:

1. An applicator for lotions comprising two layers of flexible material joined together in a manner to allow insertion of at least a part of a user's hand between the layers, each layer having an outer surface and an inner surface, at least one of the layers comprising a flexible synthetic foam material and there being applied to the outer surface of said foam layer a layer of flock comprising an area of closely-packed fibres, each fibre being attached at one end to said outer surface of the foam layer by an adhesive so that the fibres are generally parallel and upstand from the outer surface of the foam layer, and the layer of flock including fibres having a length in the range of 0.20–1.00 mm.

2. An applicator according to claim 1, having an open edge, for the insertion of at least part of the user's hand, where the layers are not joined together, two joined side edges extending away from opposite ends respectively of the open edge, and a convexly curved joined end edge extending between the ends of the side edges remote from the open edge, the curved end edge being part-circular in shape and the side edges being tangential to the end edge so as to form smooth extensions thereof.

3. An applicator according to claim 1, wherein the layers are secured together by a method selected from stitching, adhesive, ultrasonic welding, high frequency welding, heat welding, and combinations thereof.

4. An applicator according to claim 1, wherein the foam layer has a thickness in the range of 2–6 mm.

5. An applicator for lotions comprising two layers of flexible material joined together in a manner to allow insertion of at least a part of a user's hand between the layers, each layer having an outer surface and an inner surface, at least one of the layers comprising a flexible synthetic foam material and there being applied to the outer surface of said foam layer a layer of flock comprising an area of closely-packed fibres, each fibre being attached at one end to said outer surface of the foam layer by an adhesive so that the fibres are generally parallel and upstand from the outer surface of the foam layer, and the fibres in the layer of flock having a length which is no greater than about 1.00 mm.

6. An applicator according to claim 5, having an open edge, for the insertion of at least part of the user's hand, where the layers are not joined together, two joined side edges extending away from opposite ends respectively of the open edge, and a convexly curved joined end edge extending between the ends of the side edges remote from the open edge, the curved end edge being part-circular in shape and the side edges being tangential to the end edge so as to form smooth extensions thereof.

7. An applicator according to claim 5, wherein the layers are secured together by a method selected from stitching, adhesive, ultrasonic welding, high frequency welding, heat welding, and combinations thereof.

8. An applicator according to claim 5, wherein the foam layer has a thickness in the range of 2–6 mm.

9. An applicator for lotions comprising two layers of flexible material joined together in a manner to allow insertion of at least a part of a user's hand between the layers, each layer having an outer surface and an inner surface, at least one of the layers comprising a flexible synthetic foam material and there being applied to the outer surface of said foam layer a layer of flock comprising an area of closely-packed fibres, each fibre being attached at one end to said outer surface of the foam layer by an adhesive so that the fibres are generally parallel and upstand from the outer surface of the foam layer, and there being applied to the inner surface of the foam layer a liquid-impermeable coating to prevent liquid migrating inwardly from the outer surface of the foam layer to an inner region of the applicator between the foam layer and the other layer of flexible material.

10. An applicator according to claim 9, having an open edge, for the insertion of at least part of the user's hand, where the layers are not joined together, two joined side edges extending away from opposite ends respectively of the open edge, and a convexly curved joined end edge extending between the ends of the side edges remote from the open edge, the curved end edge being part-circular in shape and the side edges being tangential to the end edge so as to form smooth extensions thereof.

11. An applicator according to claim 9, wherein the layers are secured together by a method selected from stitching, adhesive, ultrasonic welding, high frequency welding, heat welding, and combinations thereof.

12. An applicator according to claim 9, wherein the foam layer has a thickness in the range of 2–6 mm.

13. An applicator according to claim 9, wherein the layer of liquid-impermeable material is applied to the inner surface of the foam as a coating of a settable liquid which permeates the foam adjacent the inner surface thereof.

14. An applicator for lotions comprising two co-extensive overlying layers of flexible synthetic foam material, the layers having co-extensive peripheral edges which are joined together in a manner to allow insertion of at least a part of a user's hand between the layers, each layer having an outer surface and an inner surface, there being applied to the outer surface of each foam layer a layer of flock comprising an area of closely-packed fibres, each fibre being attached at one end to said outer surface of the foam layer by an adhesive so that the fibres are generally parallel and upstand from the outer surface of the foam layer, and each layer of flock including fibres having a length in the range of 0.20–1.00 mm.

15. An applicator according to claim 14, having an open edge, for the insertion of at least part of the user's hand, where the layers are not joined together, two joined side edges extending away from opposite ends respectively of the open edge, and a convexly curved joined end edge extending between the ends of the side edges remote from the open edge, the curved end edge being part-circular in shape and the side edges being tangential to the end edge so as to form smooth extensions thereof.

16. An applicator according to claim 14, wherein the layers are secured together by a method selected from stitching, adhesive, ultrasonic welding, high frequency welding, heat welding, and combinations thereof.

17. An applicator according to claim 14, wherein the foam layer has a thickness in the range of 2–6 mm.

18. An applicator for lotions comprising two co-extensive overlying layers of flexible synthetic foam material, the layers having co-extensive peripheral edges which are joined together in a manner to allow insertion of at least a part of a user's hand between the layers, each layer having an outer surface and an inner surface, there being applied to the outer surface of each foam layer a layer of flock comprising an area of closely-packed fibres, each fibre being attached at one end to said outer surface of the foam layer by an adhesive so that the fibres are generally parallel and upstand from the outer surface of the foam layer, and the fibres in each layer of flock having a length which is no greater than about 1.00 mm.

19. An applicator according to claim 18, having an open edge, for the insertion of at least part of the user's hand, where the layers are not joined together, two joined side edges extending away from opposite ends respectively of the open edge, and a convexly curved joined end edge extending between the ends of the side edges remote from the open edge, the curved end edge being part-circular in shape and the side edges being tangential to the end edge so as to form smooth extensions thereof.

20. An applicator according to claim 18, wherein the layers are secured together by a method selected from stitching, adhesive, ultrasonic welding, high frequency welding, heat welding, and combinations thereof.

21. An applicator according to claim 18, wherein the foam layer has a thickness in the range of 2–6 mm.

22. An applicator for lotions comprising two co-extensive overlying layers of flexible synthetic foam material, the layers having co-extensive peripheral edges which are joined together in a manner to allow insertion of at least a part of a user's hand between the layers, each layer having an outer surface and an inner surface, there being applied to the outer surface of each foam layer a layer of flock comprising an area of closely-packed fibres, each fibre being attached at one end to said outer surface of the foam layer by an adhesive so that the fibres are generally parallel and upstand from the outer surface of the foam layer, and there being applied to the inner surface of each foam layer a liquid-impermeable coating to prevent liquid migrating inwardly from the outer surface of the foam layer to an inner region of the applicator between the two foam layers.

23. An applicator according to claim 22, having an open edge, for the insertion of at least part of the user's hand, where the layers are not joined together, two joined side edges extending away from opposite ends respectively of the open edge, and a convexly curved joined end edge extending between the ends of the side edges remote from the open edge, the curved end edge being part-circular in shape and the side edges being tangential to the end edge so as to form smooth extensions thereof.

24. An applicator according to claim 22, wherein the layers are secured together by a method selected from stitching, adhesive, ultrasonic welding, high frequency welding, heat welding, and combinations thereof.

25. An applicator according to claim 22, wherein the foam layer has a thickness in the range of 2–6 mm.

26. An applicator according to claim 22, wherein the layer of liquid-impermeable material is applied to the inner surface of the foam as a coating of a settable liquid which permeates the foam adjacent the inner surface thereof.

27. An applicator for lotions comprising two co-extensive overlying layers of flexible synthetic foam material, the layers having co-extensive peripheral edges which are joined together in a manner to allow insertion of at least a part of a user's hand between the layers, each layer having an outer surface and an inner surface, there being applied to the outer surface of each foam layer a layer of flock comprising an area of closely-packed fibres, each fibre being attached at one end to said outer surface of the foam layer by an adhesive so that the fibres are generally parallel and upstand from the outer surface of the foam layer, each layer of flock including fibres having a length in the range of 0.20–1.00 mm, and there being applied to the inner surface of each foam layer a liquid-impermeable coating to prevent liquid migrating inwardly from the outer surface of the foam layer to an inner region of the applicator between the two foam layers.

28. An applicator according to claim 27, wherein the layer of liquid-impermeable material is applied to the inner surface of the foam as a coating of a settable liquid which permeates the foam adjacent the inner surface thereof.

29. An applicator for lotions comprising two co-extensive overlying layers of flexible synthetic foam material, the layers having co-extensive peripheral edges which are joined together in a manner to allow insertion of at least a part of a user's hand between the layers, each layer having an outer surface and an inner surface, there being applied to the outer surface of each foam layer a layer of flock comprising an area of closely-packed fibres, each fibre being attached at one end to said outer surface of the foam layer by an adhesive so that the fibres are generally parallel and upstand from the outer surface of the foam layer, the fibres in each layer of flock having a length which is no greater than about 1.00 mm, and there being applied to the inner surface of each foam layer a liquid-impermeable coating to prevent liquid migrating inwardly from the outer surface of the foam layer to an inner region of the applicator between the two foam layers.

30. An applicator according to claim 29, wherein the layer of liquid-impermeable material is applied to the inner surface of the foam as a coating of a settable liquid which permeates the foam adjacent the inner surface thereof.

* * * * *